United States Patent
Kanno

[11] Patent Number: 5,957,685
[45] Date of Patent: Sep. 28, 1999

[54] TWISTER FOR LIGATURE WIRE

[75] Inventor: Yoneo Kanno, Nagareyama, Japan

[73] Assignee: Kazuyuki Higurashi (Partial Interest), Matsudo, Japan

[21] Appl. No.: 09/003,639

[22] Filed: Jan. 7, 1998

[30] Foreign Application Priority Data

Jan. 16, 1997 [JP] Japan .................................. 9-017934

[51] Int. Cl.$^6$ .............................. A61C 3/00; B21F 9/02
[52] U.S. Cl. .............................. 433/3; 433/141; 140/93.6
[58] Field of Search .................................. 433/3, 2, 153, 433/156, 162, 141, 146; 140/93.6, 149

[56] References Cited

U.S. PATENT DOCUMENTS

| | | | |
|---|---|---|---|
| 2,425,871 | 8/1947 | Eichorst | 140/149 |
| 2,682,063 | 6/1954 | Miloche | 433/3 |
| 3,163,187 | 12/1964 | MacIntosh | 140/93.6 |
| 3,273,605 | 9/1966 | Ferrara | 140/93.6 |
| 3,420,280 | 1/1969 | Allyn | 140/149 |
| 3,596,357 | 8/1971 | Matsumoto | 433/3 |
| 3,759,302 | 9/1973 | Attenborough | 433/3 |
| 5,004,020 | 4/1991 | Meinershagen | 140/93.6 |
| 5,125,830 | 6/1992 | Reinhard et al. | 433/3 |

*Primary Examiner*—John J. Wilson
*Assistant Examiner*—Patrick A. Hilsmier
*Attorney, Agent, or Firm*—Oblon, Spivak, McClelland, Maier, & Neustadt, P.C.

[57] ABSTRACT

A twister for orthodontic ligature wires which easily enable a twisting operation of the wire with one hand, and is capable of clamping the wire with certainty, and simple in construction. The twister for passing the ligature wire in a nipping cylinder and a gripping cylinder to nip the wire, comprises a guide hole provided in the nipping cylinder to enable inserting the wire in a direction along a central axis of the nipping cylinder, an insertion port provided at a tip end of the guide hole, a compartment pin for inhibition of twisting provided on the insertion port, or an engagement piece provided on an extension of the insertion port, and a locking mechanism mounted in the nipping cylinder and the gripping cylinder to allow engagement and disengagement of the wire with one hand.

7 Claims, 4 Drawing Sheets

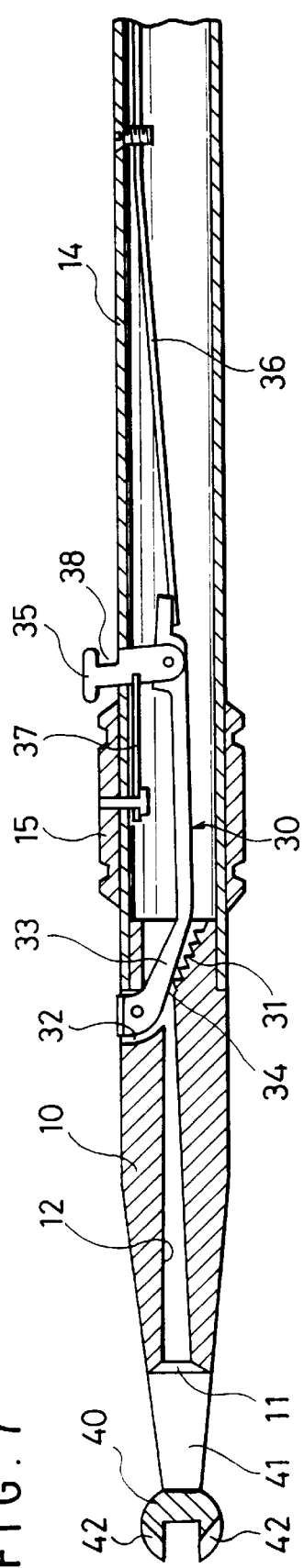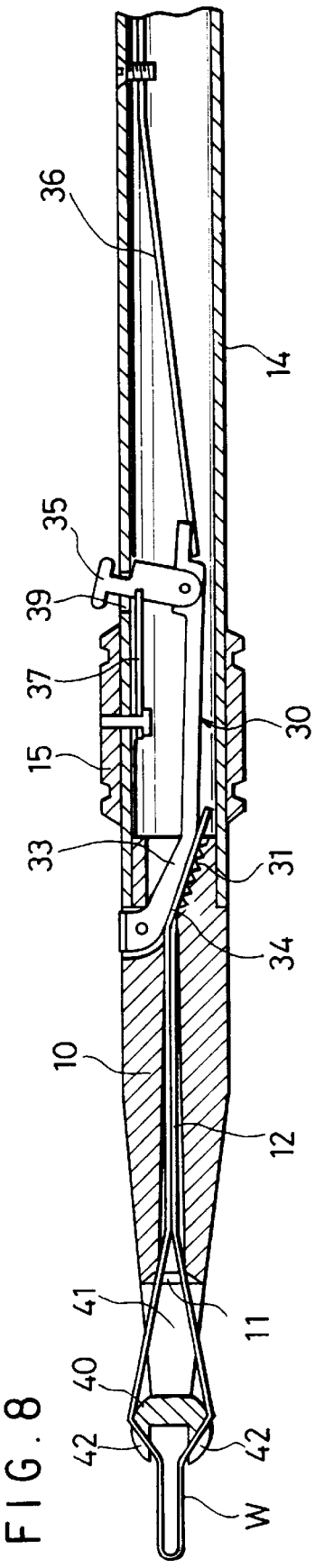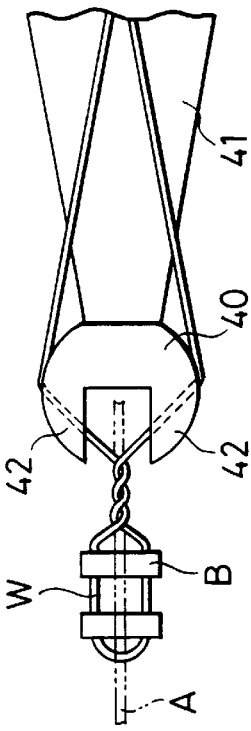

TWISTER FOR LIGATURE WIRE

BACKGROUND OF THE INVENTION

The present invention relates to a twister for orthodontic ligature wires, which is used in orthodontics to bind an arch wire to brackets attached to a tooth or teeth.

DESCRIPTION OF THE RELATED ART

A conventional twister for orthodontic ligature wires is well known which comprises a pair of nipping rods pivotally mounted to each other to be in the form of pinchers and allows one hand to grasp a gripping portion of the twister to enable a nipping portion on a tip end of the twister to nip a wire near a bent portion of the wire to twist the wire in the mouth.

Also, a twister for binding of a short wire is well known which is made in the form of ever-sharp pencil and allows a preform wire to be inserted axially therein for nipping, and bound through rotation of a gripping portion thereof.

The conventional twister described above has a drawback in that it is difficult due to construction to perform twisting of a wire in the mouth while rotating the utensil with one hand in a state, in which the wire is nipped, and to clamp the wire with certainty.

The twister, described above, in the form of a continuously sharp pencil for binding of a short wire cannot be used for binding of a long wire due to the incapability of inserting a long wire thereinto and has a complex wire locking mechanism to take time in manufacture.

SUMMARY OF THE INVENTION

The present invention solves the above-described problems of conventional twisters and provides a twister which facilitates performing a twisting manipulation of a ligature wire with one hand and enables clamping the wire with certainty and which is simple in construction.

To attain the above object, a twister for orthodontic ligature wires, according to the invention, comprises a nipping cylinder having a gradually tapering forward portion and provided at a tip end thereof with a wire insertion port, the nipping cylinder being internally formed with a guide hole, which allows the wire to pass therethrough and is provided at an inner periphery of a tip end thereof with ridges, a gripping cylinder connected to a rear end of the nipping cylinder, a locking rod mounted inside the nipping cylinder and a forward portion of the gripping cylinder and having a tip end thereof engageable with the ridges, and a manual button pivotally mounted to one side of the gripping cylinder and having an end of a shaft portion thereof pivotally mounted to a rear end of the locking rod, which end can be fixed in a state, in which the tip end of the locking rod is engaged with and disengaged from the ridges.

In one aspect of the invention, the nipping cylinder has a gradually tapering forward portion and is internally formed with a guide hole, which allows a wire to be inserted axially therethrough, which is formed at a tip end thereof with an insertion port, which is provided with a compartment pin for inhibition of twisting, and a locking mechanism is mounted in the nipping cylinder for allowing engagement and disengagement of the wire in the guide hole.

In other aspect of the invention, the nipping cylinder has a gradually tapering forward portion, and is provided with an axially extending guide hole for passing of the wire therethrough, the insertion port is formed at a tip end of the guide hole and has its one side extended to provide an engagement piece for inhibition of twisting, and the locking mechanism is mounted in the nipping cylinder for allowing engagement and disengagement of the wire in the guide hole.

In further aspect of the invention, the locking mechanism comprises ridges provided on a rear end of the guide hole in the gripping cylinder, a groove provided on a side opposite to the ridges, a locking rod which is mounted to extend in the nipping cylinder and the gripping cylinder and a tip end of which is pivotally mounted in the groove, and a manual button which is mounted to the gripping cylinder and a shaft portion of which is pivotally mounted at an end thereof to a rear end of the locking rod, the manual button being enabled to be fixed in a state, in which a forward portion of the locking rod is pressed against and separated from the ridges.

In still further aspect of the invention, the locking mechanism may comprise a locking hole provided on one side of the nipping cylinder to lead to the guide hole, and a circular-shaped locking piece mounted eccentrically and pivotally in the locking hole to allow a peripheral portion thereof to partly appear and disappear in the guide hole to engage with and disengage from the wire in the guide hole, and a manual piece provided on one side of the locking piece to extend from the locking hole.

In other aspect of the invention, the locking mechanism may comprise a button hole provided in place on the nipping cylinder to be perpendicular to the guide hole, an engagement button provided in the button hole to allow the wire in the guide hole to bend and engage in the button hole, and a release button capable of disengaging the wire from said button hole.

In further aspect of the invention, the locking mechanism may comprise a circular-shaped locking piece rotatably mounted at the rear end of the nipping cylinder within the gripping cylinder and provided therein with a through hole, which allows communication to the guide hole in a linear fashion, a manual piece projectingly provided on one side of the locking piece, a manual ring fitted on an outer periphery of the gripping cylinder and engaged with the manual piece, the manual ring being adapted to move forward and rearward to turn the locking piece to enable the wire inserted through the guide hole and the through hole to bend and engage, and a stopper provided on one side of the nipping cylinder to be engageable with a tip end of the manual ring so that the locking piece can maintain a wire locking condition.

In a still further aspect of the invention, the locking mechanism comprises a recess provided in place on the guide hole, a groove provided on a side opposite to the recess to lead outside the nipping cylinder, a locking rod pivotally mounted at a forward portion of the gripping cylinder, an engagement piece provided at a tip end of the locking rod to be disposed in the groove to enable entering into the recess, and a push button pivotally mounted at a tip end thereof to a rear end of the locking rod and having a head thereof projecting outside the gripping cylinder, and wherein manipulation of the push button allows the wire to engage and disengage between the recess and the engagement piece and allows the locking rod to be maintained in an engaged state.

In other aspect of the invention, the guide hole extends along a central axis of the nipping cylinder to pass the ligature wire therethrough, the insertion port is formed at the tip end of the guide hole, the engagement piece is provided on the extension on one side of the insertion port for inhibition of twisting, the locking mechanism is mounted on the periphery of the nipping cylinder to enable the wire in the guide hole to engage and disengage, the gripping cylinder is connected to the rear end of the nipping cylinder, and a groove is provided on one sides of the nipping cylinder and the gripping cylinder to allow the wire to be charged into the guide hole from laterally.

A twister for orthodontic ligature wires, according to the invention, has both ends of a lengthy wire extended in a nipping cylinder and a gripping cylinder, and comprises the nipping cylinder having a gradually tapering forward portion and provided at a tip end thereof with a wire insertion port, the nipping cylinder being internally formed with a guide hole, which allows the wire to pass therethrough and is provided at an inner periphery of a tip end thereof with ridges, the gripping cylinder connected to a rear end of the nipping cylinder, a locking rod mounted inside the nipping cylinder and a forward portion of the gripping cylinder and having a tip end thereof engageable with the ridges, and a manual button pivotally mounted to one side of the gripping cylinder and having an end of a shaft portion thereof pivotally mounted to a rear end of the locking rod, which end can be fixed in a predetermined state, in which the tip end of the locking rod is engaged with and disengaged from the ridges.

In some cases, the nipping cylinder has a gradually tapering forward portion, the guide hole for passing of the wire therethrough, is formed axially in the nipping cylinder, the insertion port is formed at a tip end of the guide hole and provided with a compartment pin for inhibition of twisting, and the locking mechanism is mounted in the nipping cylinder for allowing engagement and disengagement of the wire in the guide hole.

Alternatively, in place of the compartment pin for inhibition of twisting, an engagement piece for inhibition of twisting may be provided on an extension of the insertion port one side thereof.

Thus, the locking mechanism comprises ridges provided on a rear end of the guide hole in the nipping cylinder, a groove provided on a side opposite to the ridges, a locking rod which is mounted to extend in the nipping cylinder and the gripping cylinder and a tip end of which is pivotally mounted in the groove, and a manual button which is mounted to the gripping cylinder and a shaft portion of which is pivotally mounted at an end thereof to a rear end of the locking rod, the manual button being enabled to be fixed in a state, in which a forward portion of the locking rod is pressed against and separated from the ridges.

Also, a circular-shaped lock piece may be provided at the rear end of the nipping cylinder within the gripping cylinder and provided therein with a through hole, which allows communication to the guide hole in a linear fashion, so that turning the lock piece causes restraining the wire.

Further, the locking mechanism may be constructed to allow bending and engaging of the wire in the guide hole with a tip end of a push button mounted in the nipping cylinder.

Also, the locking mechanism may be constructed to allow a push button to operate the locking piece pivotally mounted in the gripping cylinder to effect bending and engagement of the wire in the guide hole with an engagement piece provided at a tip end of the locking rod.

Further, in some cases, a groove is provided on one sides of the nipping cylinder and the gripping cylinder to allow the wire to be charged into the guide hole from laterally.

BRIEF DESCRIPTION OF THE DRAWINGS

The invention, together with objects and advantages thereof, may best be understood by reference to the following description of the presently preferred embodiments together with the accompanying drawings in which:

FIG. 7 is a side cross sectional view of a third embodiment of the invention;

FIG. 8 is a side cross sectional view of the third embodiment in use;

FIG. 9 is a schematic view illustrating a twisted condition;

DESCRIPTION OF THE PREFERRED EMBODIMENTS

Embodiments of the invention will be described with reference to the accompanying drawings.

First Embodiment

Figure 1:
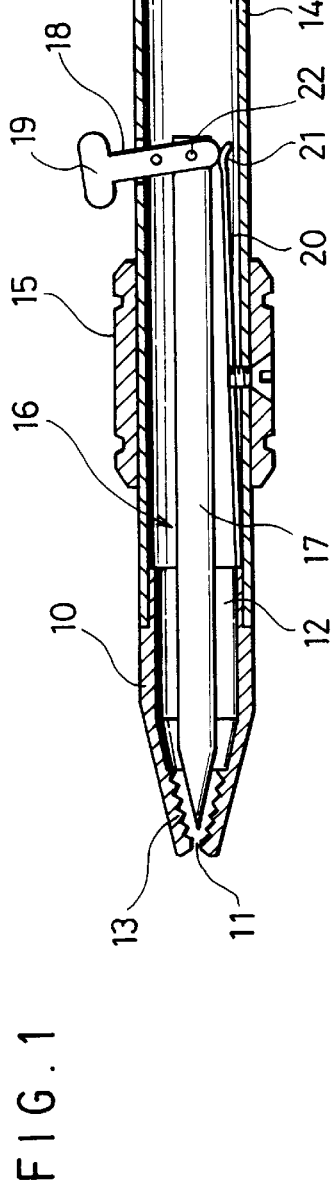
FIG. 1 is a side cross sectional view of a first embodiment of the invention.
Figure 2:
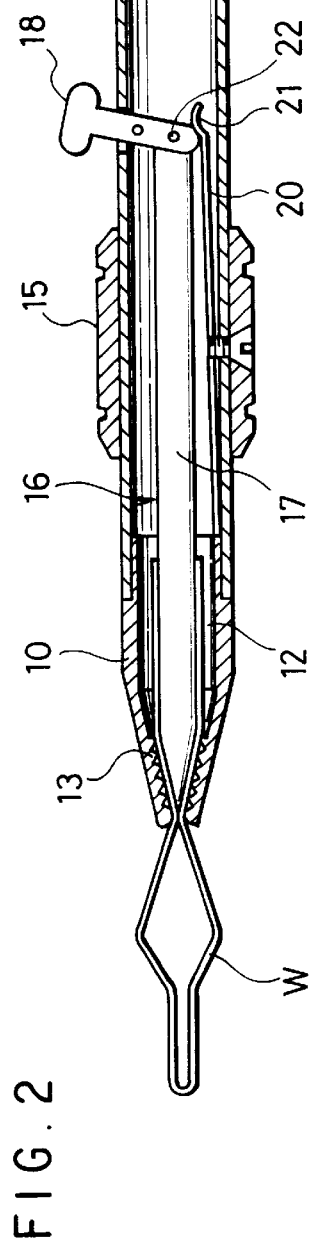
FIG. 2 is a side cross sectional view of the first embodiment in use.

In a first embodiment shown in FIGS. 1 and 2, the reference numeral 10 designates a nipping cylinder, a forward portion of which tapers gradually, a tip end of which is provided with a wire insertion port 11, and inside which a guide hole 12 is formed to pass wires therethrough, and annular ridges 13 are formed on an inner periphery of a tip end of the guide hole 12. The nipping cylinder is connected at its rear end to an elongated gripping cylinder 14. Reference numeral 15 designates a slide-proof band mounted outside of the gripping cylinder 14.

Reference numeral 16 designates a wire locking mechanism having a locking rod 17, a tip end of which is sharpened at an acute angle to match the annular ridges 13 in the guide hole 12 and a rear end of which is pivotally mounted to an end of a shaft portion of a manual button 18 which in turn is pivotally mounted in the gripping cylinder 14 to be rotatable.

Thus, when a head 19 of the manual button 18 protruding from the gripping cylinder 14 is turned forward and rearward, the locking rod 17 is moved a predetermined distance forward and rearward to allow a tip end of the locking rod to engage with or disengage from the annular ridges 13.

Reference numeral 20 designates a stopper form of a leaf spring, which is mounted below the locking rod in the gripping cylinder 14 to resiliently support a lower end of the shaft portion of the manual button 18 and a tip end of which is formed with a bent portion 21 adapted to engage with or disengage from the lower end of the shaft portion of the manual button 18 in a state, in which the operating button 18 turns forward and rearward. Thus engagement of the bent portion 21 with the lower end of the shaft portion of the manual button 18 allows the manual button 18 to stop at its turning position.

When the twister is to be used, both ends of the ligature wire W are inserted into the guide hole 12 through the insertion port 11 to extend through the gripping cylinder 14. Thus pushing the head 19 of the manual button 18 rearward with a finger moves the locking rod 17 forward, so that the ligature wire W is interposed between the locking rod 17 and the annular ridges 13 to be locked.

Figure 3:
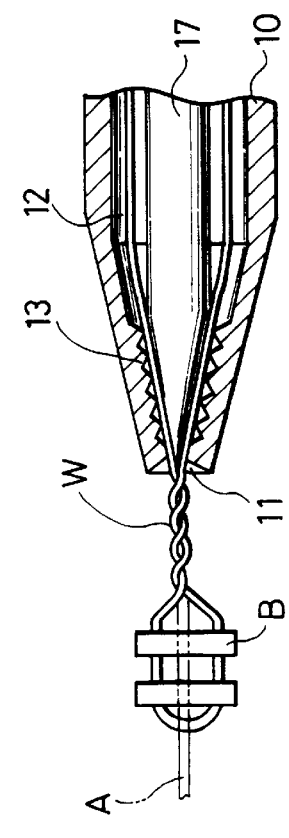
FIG. 3 is a schematic view illustrating a twisted condition.

As shown in FIG. 3, an inverted U-shaped portion of the wire W nips brackets B attached to a tooth or teeth being subjected to orthodontic treatment, and then the gripping cylinder 14 is rotated to twist the wire W, so that an arch wire A stretched between teeth is bound to the brackets B. After a twisting work is completed, pushing the manual button 18 forward moves the locking rod 17 rearward to unlock the wire W.

Second Embodiment

Figure 4:
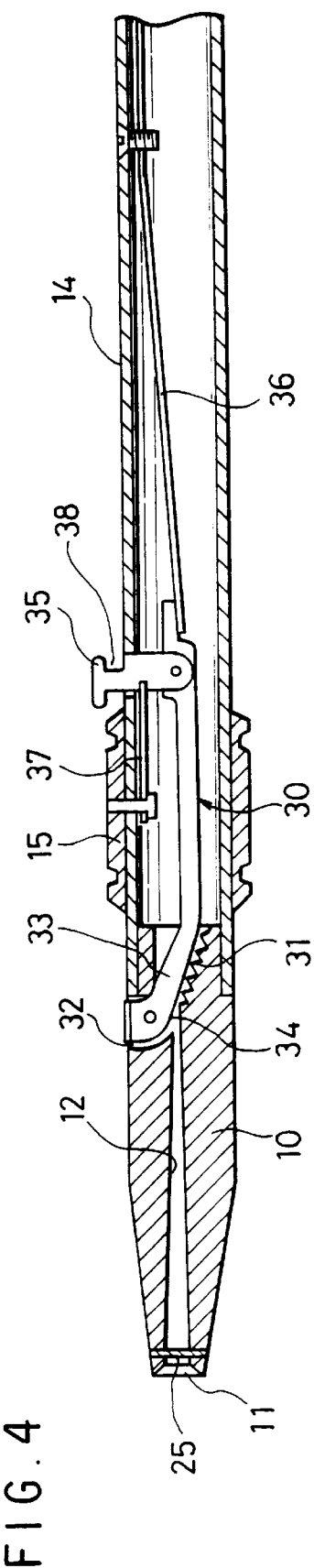
FIG. 4 is a side cross sectional view of a second embodiment of the invention.
Figure 5:
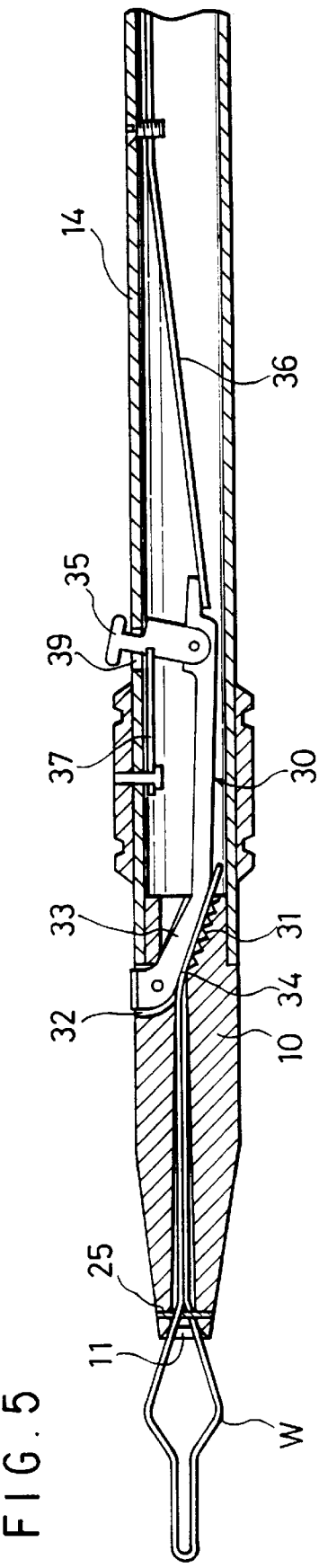
FIG. 5 is a side cross sectional view of the second embodiment in use.

In a second embodiment shown in FIGS. 4 and 5 formed at a tip end of the guide hole 12 is an insertion port 11 which is provided with a compartment pin 25 for inhibition of twisting, and mounted in the nipping cylinder is a locking mechanism 30 capable of having the wire engaged and disengaged in the guide hole.

The locking mechanism 30 comprises ridges 31 formed over an inclined surface where a rear end of a guide hole 12 of a nipping cylinder 10 is inclined downwardly, the ridges 31 being oriented perpendicular to the guide hole 12, and a groove 32 provided on a side opposite to the ridges.

Reference numeral 33 designates a locking rod provided to extend in the nipping cylinder and the gripping cylinder, and formed at its forward portion with a pressing portion 34, which can contact with the ridges 31 and a tip end of which is pivotally mounted in a groove 32 to allow the pressing portion 34 to abut against the ridges 31 when turned. Pivotally mounted to a rear end of the locking rod 33 is a shaft end of a push button 35, a head of which protrudes outside the gripping cylinder.

Reference numeral 36 designates a leaf spring provided to constantly bias the rear end of the locking rod 33 upward. Reference numeral 37 designates a stopper mounted on a forward portion of the push button 35 in the gripping cylinder such that its vertically bending spring piece is latched at its rear end by the forward portion of a shaft of the push button 35 to resiliently support the push button 35 rearward.

Figure 6:
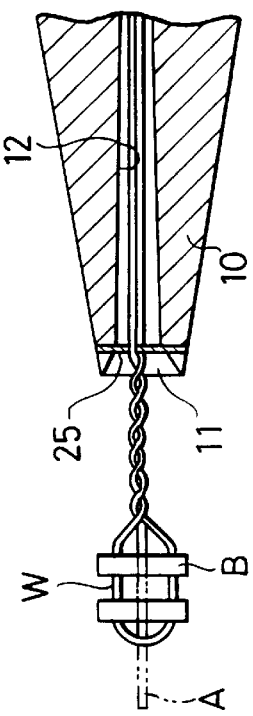
FIG. 6 is a schematic view illustrating a twisted condition.

When the twister is to be used, both ends of the ligature wire W are passed over either side of the compartment pin 25 as shown in FIG. 6 to be inserted into the guide hole 12 through the insertion port 11 to extend in the gripping cylinder. A notch 38 provided on the shaft portion of the push button 35 engages with a peripheral edge of a through hole 39 on the gripping cylinder and is biased rearward by the stopper 37, so that the wire interposed between the ridges 31 and the pressing portion 34 can be maintained in a locked position.

After a twisting work is completed, pushing the push button 35 forward disengages the notch 38 from the peripheral edge of the through hole 39 and turns the locking rod 33 upward to unlock the wire W.

Third Embodiment

In a third embodiment shown in FIGS. 7 and 8, instead of the compartment pin 25 for inhibition of twisting in the second embodiment, an insertion port is extended as shown by the reference number 41 to provide an engagement piece 40. The reference numeral 42 designates engagement grooves provided on a tip end of the engagement piece 40. The remaining constitution of the third embodiment is the same as that of the second embodiment.

When the twister is to be used, the inverted U-shaped portion of the ligature wire W are made as shown in FIG. 9 to bridge over and engage with the both engagement grooves 42, 42 on the engagement piece 40, and both ends of the wire are inserted into the guide hole 12 through the insertion port 11 to extend in the gripping cylinder 14 to allow a twisting work in a locked condition.

Fourth Embodiment.

A fourth embodiment is the same in terms of constitution as the third embodiment except a wire locking mechanism, and so only differences in constitution will be described hereinbelow.

Figure 10:
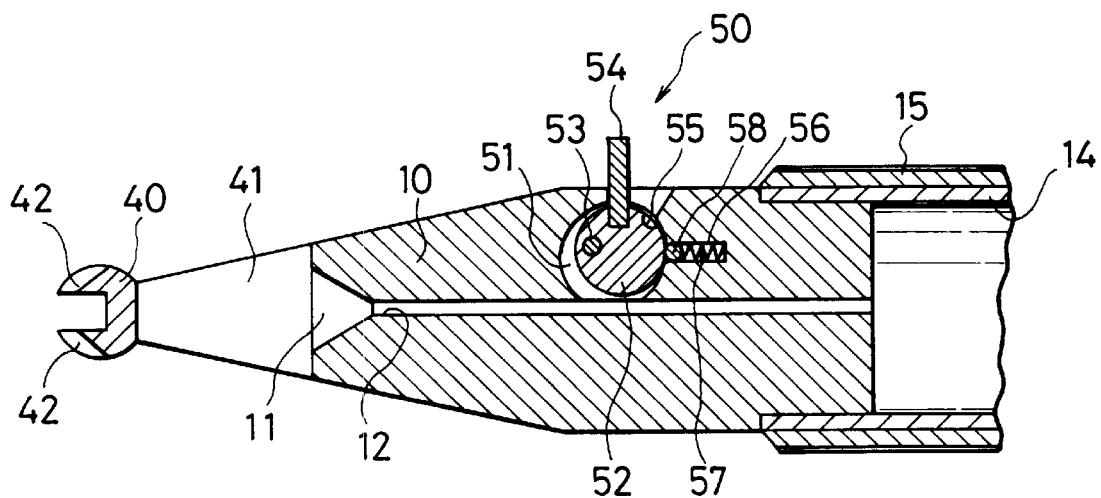
FIG. 10 is a side cross sectional view of a fourth embodiment of the invention.
Figure 11:
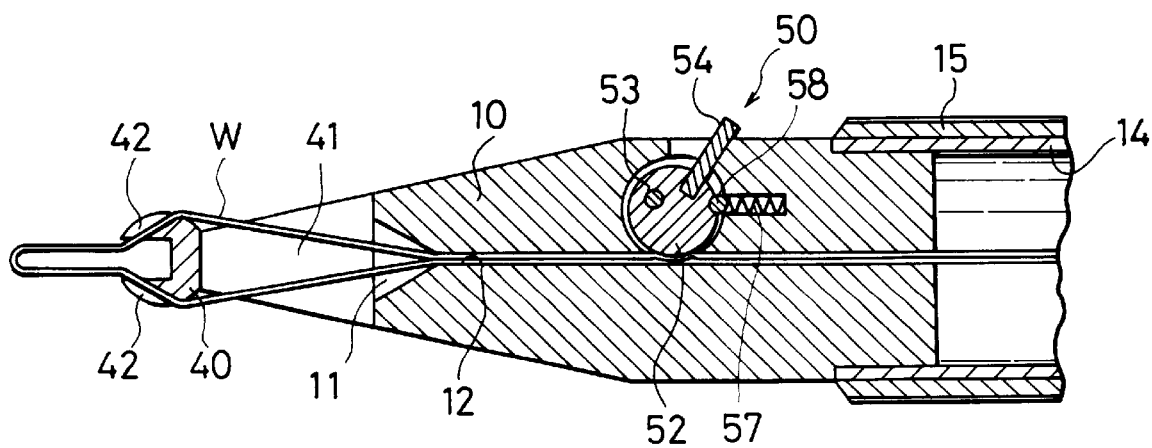
FIG. 11 is a side cross sectional view of the fourth embodiment in use.

As shown in FIGS. 10 and 11, a locking mechanism 50 comprises a locking hole 51 formed on one side of a nipping cylinder 10 to lead to a guide hole 12, and a locking piece 52 eccentrically mounted at a pivot 53 in the locking hole 51 in such a manner to allow its lower portion to appear and disappear in the guide hole 12.

Further, the locking piece 52 is provided at a top end thereof with a manual piece 54 and on a periphery thereof with an arcuate engagement hole 55. A ball 58 biased by a spring 57 received in a recess 56 provided on one side of the locking hole 51 can be fitted into the engagement hole 55.

In the twister according to the embodiment, when falling the manual piece 54 rearward turns the locking piece 52 a predetermined angle, a lower end of the locking piece projects into the guide hole 12 to restrain the wire W passed through the guide hole 12 to lock the same, and the ball 58 fits into the engagement hole 55 to secure the locking piece 52 for maintaining of a locked state.

The present examples and embodiments are to be considered as illustrative and not restrictive and the invention is not to be limited to the details given herein, but may be modified within the scope and equivalence of the appended claims.

What is claimed is:

1. A twister for orthodontic ligature wires, comprising a nipping cylinder having a gradually tapering forward portion and provided at a tip end thereof with a wire insertion port, said nipping cylinder being internally formed with a guide hole, which allows a wire to pass therethrough and being provided at an inner periphery of a tip end thereof with ridges, a gripping cylinder connected to a rear end of said nipping cylinder, a locking rod mounted inside said nipping cylinder and at a forward portion of said gripping cylinder and having a tip end thereof engageable with said ridges, and a manual button pivotally mounted to one side of said gripping cylinder and having an end of a shaft portion thereof pivotally mounted to a rear end of said locking rod, which end can be fixed in a state, in which the tip end of said locking rod is engaged with and disengaged from said ridges.

2. A twister for orthodontic ligature wires, comprising a nipping cylinder having a gradually tapering forward portion, a guide hole for passing of the wire therethrough, formed axially in said nipping cylinder, an insertion port formed at a tip end of said guide hole and provided with a compartment pin for inhibition of twisting, a gripping cylinder connected to a rear end of said nipping cylinder, and a locking mechanism mounted in said nipping cylinder for allowing engagement and disengagement of the wire in said guide hole.

3. A twister for orthodontic ligature wires, comprising a nipping cylinder having a gradually tapering forward portion, a guide hole for passing of the wire therethrough, formed axially in said nipping cylinder, an insertion port formed at a tip end of said guide hole, an engagement piece provided on an extension of one side of said insertion port for inhibition of twisting, a gripping cylinder connected to a rear end of said nipping cylinder, and a locking mechanism mounted in said nipping cylinder for allowing engagement and disengagement of the wire in said guide hole.

4. The twister according to claim 2, wherein said locking mechanism comprises ridges provided on a rear end of said guide hole in said nipping cylinder, a groove provided on a side opposite to said ridges, a locking rod which is mounted to extend in said nipping cylinder and said gripping cylinder and a tip end of which is pivotally mounted in said groove, and a manual button which is mounted to said gripping cylinder and a shaft portion of which is pivotally mounted at an end thereof to a rear end of said locking rod, said manual button being enabled to be fixed in a state, in which a forward portion of said locking rod is pressed against and separated from said ridges.

5. The twister according to claim 3, wherein said locking mechanism comprises ridges provided on a rear end of said guide hole in said nipping cylinder, a groove provided on a side opposite to said ridges, a locking rod which is mounted to extend in said nipping cylinder and said gripping cylinder and a tip end of which is pivotally mounted in said groove, and a manual button which is mounted to said gripping cylinder and a shaft portion of which is pivotally mounted at an end thereof to a rear end of said locking rod, said manual button being enabled to be fixed in a state, in which a forward portion of said locking rod is pressed against and separated from said ridges.

6. The twister according to claim 2, wherein said locking mechanism comprises a locking hole provided on one side of said nipping cylinder to lead to said guide hole, a circular-shaped locking piece mounted eccentrically and pivotally in said locking hole to allow a peripheral portion thereof to partly appear and disappear in said guide hole to engage with and disengage from the wire in said guide hole, and a manual piece provided on one side of said locking piece to extend from said locking hole.

7. The twister according to claim 3, wherein said locking mechanism comprises a locking hole provided on one side of said nipping cylinder to lead to said guide hole, a circular-shaped locking piece mounted eccentrically and pivotally in said locking hole to allow a peripheral portion thereof to partly appear and disappear in said guide hole to engage with and disengage from the wire in said guide hole, and a manual piece provided on one side of said locking piece to extend from said locking hole.

* * * * *

UNITED STATES PATENT AND TRADEMARK OFFICE
CERTIFICATE OF CORRECTION

PATENT NO. : 5,957,685

DATED : September 28, 1999

INVENTOR(S): Yoneo KANNO

It is certified that an error appears in the above-identified patent and that said Letters Patent is hereby corrected as shown below:

On the title page, item [30], should be:

--[30] Foreign Application Priority Data

Jan. 16, 1997    [JP] Japan.........9-017934
    Dec. 16, 1997    [JP] Japan.........9-363260--

Signed and Sealed this

Twenty-third Day of May, 2000

Attest:

Q. TODD DICKINSON

*Attesting Officer*    *Director of Patents and Trademarks*